United States Patent
Clevenger et al.

(10) Patent No.: US 9,655,992 B2
(45) Date of Patent: May 23, 2017

(54) SURFACE MODIFIED BIOLOGICAL MATERIALS

(75) Inventors: Randell Clevenger, North Plainfield, NJ (US); Rong Dong, East Brunswick, NJ (US); Jordan Katz, Short Hills, NJ (US)

(73) Assignee: Orthobond, Inc., North Brunswick, NJ (US)

( * ) Notice: Subject to any disclaimer, the term of this patent is extended or adjusted under 35 U.S.C. 154(b) by 601 days.

(21) Appl. No.: 13/458,156

(22) Filed: Apr. 27, 2012

(65) Prior Publication Data

US 2012/0294953 A1 Nov. 22, 2012

Related U.S. Application Data

(60) Provisional application No. 61/479,627, filed on Apr. 27, 2011.

(51) Int. Cl.
| | | |
|---|---|---|
| *A61K 35/12* | (2015.01) | |
| *A61K 38/39* | (2006.01) | |
| *A61K 47/48* | (2006.01) | |
| *A61K 38/17* | (2006.01) | |
| *C07K 1/00* | (2006.01) | |
| *C07K 16/00* | (2006.01) | |
| *C07K 17/00* | (2006.01) | |
| *C09H 1/00* | (2006.01) | |
| *A61L 27/24* | (2006.01) | |
| *A61L 27/54* | (2006.01) | |

(52) U.S. Cl.
CPC .............. *A61L 27/24* (2013.01); *A61L 27/54* (2013.01)

(58) Field of Classification Search
None
See application file for complete search history.

(56) References Cited

U.S. PATENT DOCUMENTS

| | | |
|---|---|---|
| 3,057,739 A | 3/1960 | Forkner |
| 5,171,574 A | 12/1992 | Kuberasampath et al. |
| RE39,192 E * | 7/2006 | MacPhee .................. 424/198.1 |
| 7,726,319 B1 | 6/2010 | Boyce |
| 2004/0187877 A1 | 9/2004 | Badylak et al. |
| 2007/0005140 A1 | 1/2007 | Kim et al. |
| 2007/0212386 A1 | 9/2007 | Patravale et al. |
| 2008/0131522 A1* | 6/2008 | Liu et al. ...................... 424/583 |
| 2008/0274184 A1* | 11/2008 | Hunt ............................. 424/484 |
| 2009/0104474 A1 | 4/2009 | Schwartz et al. |
| 2009/0155335 A1* | 6/2009 | O'Shaughnessey et al. . 424/423 |
| 2010/0317080 A1* | 12/2010 | Zimmermann et al. ... 435/173.1 |
| 2011/0056882 A1* | 3/2011 | Borenstein et al. ..... 210/321.62 |
| 2011/0110986 A1 | 5/2011 | Schwartz et al. |

FOREIGN PATENT DOCUMENTS

| | | |
|---|---|---|
| WO | 0047130 | 8/2000 |
| WO | WO 2008101566 A2 * | 8/2008 |
| WO | 2009105760 | 8/2009 |

OTHER PUBLICATIONS

Lee 'Atomic Layer Deposition on Biological Matter,' Dissertation [online], Dec. 24, 2009 [retrieved on Nov. 25, 2014]. Retrieved from the internet: http://d-nb.info/999966138/34.*
Adden et al. Langmuir, vol. 22, No. 19, Sep. 12, 2006, p. 8197-8204.*
International Search Report for International Patent Application No. PCT/US2012/035515 issued Jul. 27, 2012, 2 pgs.
International Search Report for International Patent Application No. PCT/US2012/035468 issued Jul. 20, 2012, 4 pgs.
Boscariol et al., Sterilization by pure oxygen plasma and by oxygen-hydrogen peroxide plasma: An efficacy study, International Journal of Pharmaceuticals, 235, 2008, pp. 170-175, Elsevier, New York.
Cheruthazhekatt et al., Gas plasmas and plasma modified materials in medicine, Journal of Applied Biomedicine, 8:55-56, 2010, pp. 55-66.
Moreira et al., Sterilization by oxygen plasma, Applied Surface Science, 235, 2004, pp. 151-155, Elsevier, New York.

* cited by examiner

*Primary Examiner* — Chris R Tate
*Assistant Examiner* — Douglas F White
(74) *Attorney, Agent, or Firm* — Lowenstein Sandler LLP

(57) ABSTRACT

Disclosed in certain embodiments is a composition comprising a biological material and transition metal atoms selected from the group consisting of Group IVB, Group VB, Group VIB of the Periodic Chart and a combination thereof, bound to a surface of the biological material.

25 Claims, 8 Drawing Sheets though not limited to, covalent bonding, ionic bonding, hydrogen bonding, dipole-dipole interactions, electrostatic interactions, dispersion forces, or a combination thereof.

SURFACE MODIFIED BIOLOGICAL MATERIALS

CROSS-REFERENCE TO RELATED APPLICATIONS

This application claims priority to U.S. provisional application No. 61/479,627 filed Apr. 27, 2011, the disclosure of which is hereby incorporated by reference in its entirety.

FIELD OF THE INVENTION

The presently disclosed subject matter includes compositions comprising biological material with pharmacologically active agent(s) bound to a surface thereof, either directly or through intermediary layers, and methods for producing said compositions.

BACKGROUND

It is desirable to alter the surface chemistry of tissue and other biological materials in order to control the body's interaction with it after implantation or grafting. One reason is to prevent infection. Another is to reduce inflammatory response.

In some cases, alteration of surface chemistry can be achieved by soaking the material in a compatible solution of a pharmacological agent. A number of issues arise from this approach. Once implanted, the pharmacological solution will diffuse from the material into the patient. Generally speaking, a higher concentration that is necessary for local efficacy must be used due to this diffusion effect. The surgeon must therefore balance the total dosage of pharmacological agent with the necessary amount required to have the desired local effect. In some cases, concentration level required may cause undesirable side effects in the patient.

In addition, once implanted, it is impossible to control the rapid elution rate of the bioactive agent form the implanted tissue into the implant site and from there, into the patient. It is generally desirable for the bioactive agent to remain within the implanted or grafted tissue for a certain amount of time. Further, depending on the pharmacological agent, the amount required in solution for local efficacy may make the implantation or grafting procedure prohibitively expensive.

Accordingly, there remains a need in the art for biological materials suitable for implantation or grafting into living mammals, and methods of creating the same.

SUMMARY OF THE INVENTION

It is an object of certain embodiments of the present invention to provide biological materials with surface modifications to allow for conjugation with a ligand.

It is an object of certain embodiments of the present invention to provide biological materials conjugated with an antimicrobial agent.

It is an object of certain embodiments of the present invention to provide biological materials that have reduced incidence of infection upon implantation or grafting into a patient.

It is an object of certain embodiments of the present invention to provide biological materials that have improved stability and integrity upon implantation or grafting into a patient.

It is an object of certain embodiments of the present invention to provide methods of manufacturing modified biological materials as disclosed herein.

The above objects of the invention, and others, may be achieved by the present invention which in certain embodiments is directed to a composition comprising a biological material and transition metal atoms selected from the group consisting of Group IVB, Group VB, Group VIB of the Periodic Chart and a combination thereof, bound to a surface of the biological material. In certain embodiments, the invention further comprises an inorganic phosphate or an organic phosphinate or phosphonate, such as 11-hydroxyundecyl-phosphonic acid, bound to the transition metal atoms. In further embodiments, a ligand is further covalently bound to the inorganic phosphate or an organic phosphinate or phosphonate.

In certain embodiments, the transition metals are present as alkoxides, which may be, e.g., bound to the surface of the biological material at the transition metal atom. Depending on the position of the transition metal on the periodic chart, such transition metal alkoxides may have from two to six alkoxide groups. Certain embodiments may include alkoxide groups having from 2 to 4 carbon atoms, such as ethoxide, propoxide, iso-propoxide, butoxide, iso-butoxide, and tert-butoxides.

The biological material can be, e.g., collagen, tissue, or bone. In certain embodiments, the tissue is acellular dermal tissue.

In certain embodiments, the present invention is directed to a composition comprising a biological material that is optionally activated by oxygen plasma prior to contact with the transition metal atoms.

In certain embodiments, the present invention is directed to a composition comprising acellular tissue; transition metal atoms selected from the group consisting of Group IVB, Group VB, Group VIB of the Periodic Chart and a combination thereof, bound to a surface of the biological material; an inorganic phosphate or an organic phosphinate or phosphonate bound to the transition metal atoms; a coupling agent bound to the acellular tissue; and a pharmacological agent bound to the coupling agent.

In certain embodiments, the present invention is directed to a method of treating biological material comprising: contacting biological material with oxygen plasma, transition metal atoms selected from the group consisting of Group IVB, Group VB, Group VIB of the Periodic Chart and a combination thereof, and an inorganic phosphate or an organic phosphinate or phosphonate to form activated biological material. In other embodiments, a ligand can be further bound to the activated biological material.

The methods of the present invention may be carried out under vacuum, depending on the vapor pressure of the inorganic phosphate or organic phosphinate or phosphonate being applied. Inorganic phosphates or organic phosphinate or phosphonates with low vapor pressure, for example, will require a high vacuum. Alternatively, ambient temperatures may be employed. Preferably, the biological material should not be exposed to ambient moisture prior to treatment with the inorganic phosphate or organic phosphinate or phosphonate. Accordingly, in certain embodiments, a vacuum is employed to remove excess transition metal, and then again after treatment with the inorganic phosphate or organic phosphinate or phosphonate.

Where bonding is referenced herein, such bonding can be achieved through any type of chemical bond, including, without limitation, covalent bonding, polar covalent bonding, ionic bonding, hydrogen bonding, van der Waals forces and a combination thereof.

In certain embodiments, the present invention is directed to the implantation or grafting of a modified biological material as disclosed herein in a patient in need thereof.

In certain embodiments, the present invention is directed to a method of performing reconstructive surgery in a patient in need thereof comprising implanting or grafting a modified biological material as disclosed herein.

In certain embodiments, the present invention is directed to a method of administering a drug to a patient in need thereof comprising implanting or grafting a biological material conjugated with pharmacological agent or bioactive agent as disclosed herein.

In describing the present invention, the following terms are to be used as indicated below. As used herein, the singular forms "a," "an," and "the" include plural references unless the context clearly indicates otherwise. Thus, for example, reference to "a pharmacological agent" includes a single pharmacological agent as well as a mixture of two or more different pharmacological agents.

As used herein, "biological material" means any material derived in whole or in part from an organism, including, without limitation, soft tissue sources such connective and non-connective tissue. Examples of connective tissue includes, without limitation, tendons, ligaments, fascia, dermal tissue, fat, dura, pericardia, fibrous tissues and synovial membranes. Examples of non-connective tissue includes, without limitation, muscles, blood vessels and nerves. "Biological material" also includes hard tissue sources such as bone and cartilage. In certain embodiments, such materials may have been harvested from a living organism and then submitted to further processing and/or chemical treatment. The living organism could be comprised of eukaryotic or prokaryotic cells. Recombinant proteins, which can be derived from bacteria such as E. coli and are produced from recombinant DNA, can also be modified with the present invention.

"Acellular biological material" refers to biological material from which all, or substantially all, viable cells and detectable subcellular components and/or debris from cell death have been removed.

In some embodiments, the acellular biological material utilized in the present invention has a concentration of viable cells that is less that about 5%, less than about 3%, less than about 1% or less than about 0.5% of the concentration in the original biological material from which the acellular biological material was derived. In other embodiments, the acellular biological material has an amount of viable cells that is less that about 3%, less than about 1%, less than about 0.5% or less than about 0.2% of the total weight of the acellular material.

In some embodiments, the acellular biological materials utilized in the present invention comprise less than about 40%, less than about 25%, less than about 10%, or less than about 5% of nucleic acid that was present in the original cellularized biological material from which the acellular biological material was derived. In other embodiments, the acellular biological material has an amount of nucleic acid that is less than about 25%, less than about 10%, less than about 5%, or less than about 2% of the total weight of the acellular material.

"Activated biological material" refers to biological material that has been contacted with an activating agent (e.g., oxygen plasma) to provide reactive functional groups on the surface of the material.

"Pharmacological agent" or "bioactive agent" means any agent that can be bound to activated biological material. Examples of bioactive or pharmacological agents include, without limitation, (i) those of an anti-infective nature, such as antimicrobials, antibiotics, antifungals, antiseptics, disinfectants, and preservatives; (ii) immunosuppressant drugs such as glucocorticoids, antibodies, ciclosporin, tacrolimus, calcineurin inhibitors, and sirolimus; and (iii) agents to mediate and induce cellular/tissue growth such as bone morphogenic proteins (BMP), epidermal growth factor (EGF), fibroblast growth factor (FGF), platelet-derived growth factor (PDGF), insulin-like growth factor (IGF-I and II), TGF-D, and vascular endothelial growth factor (VEGF).

"Anti-infective" refers to anything that is capable of destroying or inhibiting the microorganism growth, including, without limitation, antimicrobial agents such as antibacterial and antifungal agents.

"Coupling agent" means an agent capable of forming a bond between the surface of an activated biological material and a ligand (such as a pharmacological or bioactive agent). This bond may be achieved by first forming a bond between the surface of the activated biological material and the coupling agent, and then forming a bond between the coupling agent and the ligand. In other embodiments, the ligand can be bonded to the coupling agent, and the resultant conjugate is bound to the biological material. Alternatively, the coupling agent may facilitate bonding directly between the surface of an activated biological material and the ligand.

The term "oxygen plasma" means an oxygen source having a portion of the molecules ionized.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

DETAILED DESCRIPTION

Figure 1:
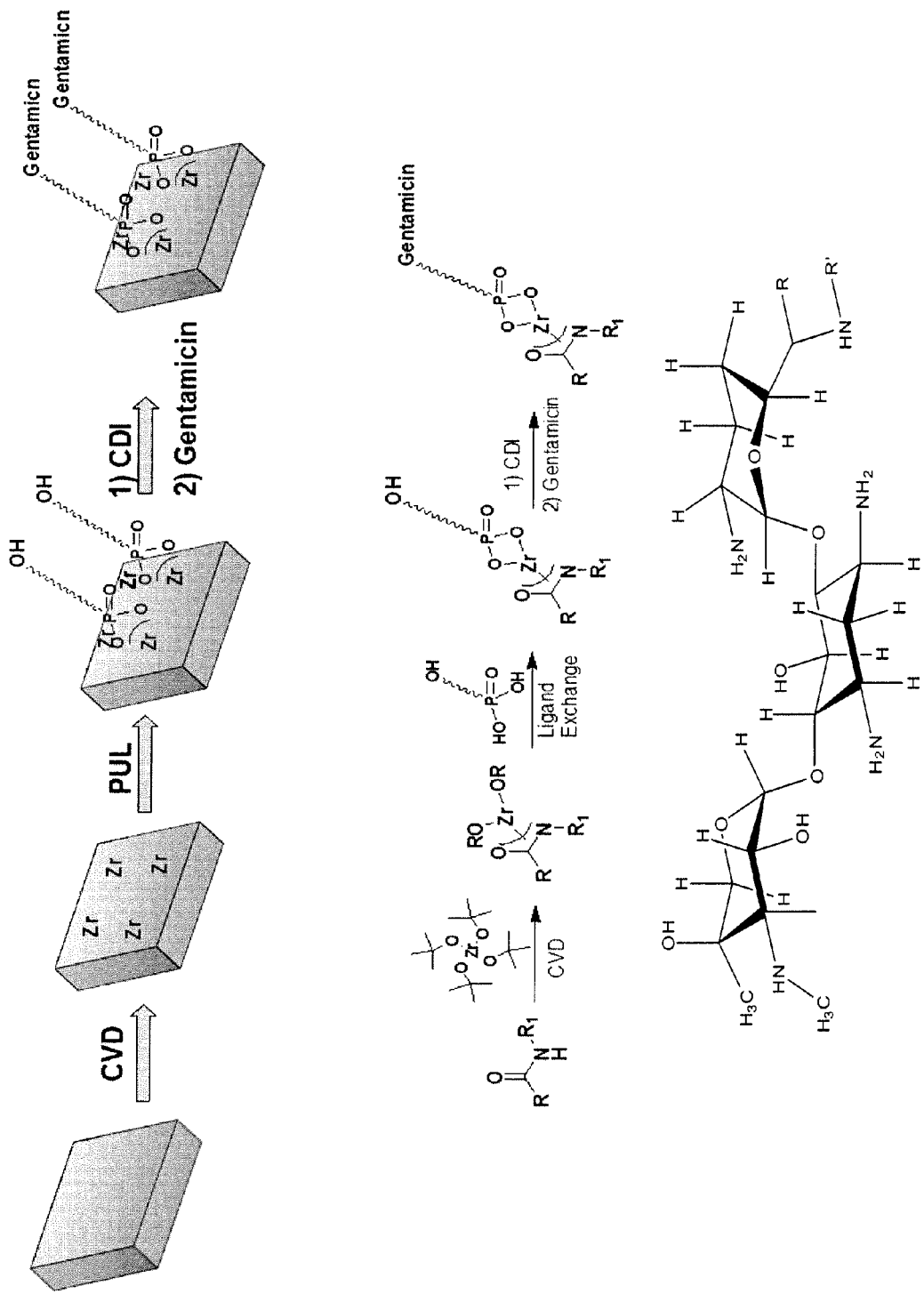
FIG. 1 depicts a schematic diagram of one embodiment of the method of the present invention.

Harvested biological material is often utilized for implantation or grafting in a host organism for a variety of reasons such as reconstructive surgery (e.g., hernia repair or external burn treatment). A common source of biological material is dermal tissue. The source of the dermal tissue can be from another area of the patient's body, called an autograft, obtained from another person (e.g., donor skin from cadavers called an allograft, or from an animal (e.g., porcine or bovine source), called a xenograft.

Implanted or grafted biological material is susceptible to complications (e.g., infection) which can lead to failure of the procedure and issues to the patient. Accordingly, it is desirable to have the biological material functionally modified (e.g. conjugated or bound to an anti-infective agent) prior to implantation or grafting.

In certain embodiments, the biological material is animal tissue. Animal tissue is mainly made of Type I collagen, which contains a very limited number of functional groups for bioconjugation (approximately 5%). In instances where it is desirable for these tissues to be processed, altered or derivitized for implantation or grafting into an organism, this lack of functional groups can present challenges. For example, it may desirable to treat implanted tissues with antibiotic agents prior to implantation to prevent infection at the surgery site. However, the lack of functional groups to which these agents can bind makes it difficult for the tissue to retain the agents long enough for the agents to impart the desired effect—i.e., preventing infection.

The present invention provides a solution to this problem by creating functional groups on the surface of biological material after exposure to one or more transition metals. Preferably, the transition metal comprises transition metal atoms selected from one or more of Group IVB, Group VB, and Group VIB of the periodic table, or compounds or combinations thereof, such as titanium, zirconium, and a combination thereof. In certain embodiments, the transition metal can be bound to the biological material via chemical vapor deposition or through solution phase applications.

In certain embodiments, the transition metal is further treated with an inorganic phosphate or an organic phosphinate or phosphonate, such as 11-hydroxyundecyl-phosphonic acid or any other phosphinate or phosphonate with an amenable functional group on the distal end of the alkyl chain. Such inorganic phosphate or organic phosphinate or phosphonate may be bound (e.g., covalently bound) to the transition metal. The inorganic phosphate or organic phosphinate or phosphonate provides free hydroxyl functional groups that are available for covalent bonding with ligands, such as antimicrobial and antibiotic agents. Preferably, this treatment does not disrupt the integrity of the bulk tissue underneath, presenting minimal challenges to post-implant integration.

One method of the present invention involves contacting a biological material with oxygen plasma to, for example, remove the water shell that is tightly associated with the biological material. The biological material is then treated with a transition metal followed by an inorganic phosphate or an organic phosphinate or phosphonate to create an activated biological material having free hydroxyl functional groups on its surface that are available for covalent bonding with ligands. The activated biological material is then thermoset.

The thermoset step can, for example, be carried out by heat, radiation, or chemical reaction. In certain embodiments, the thermoset step can be carried at a temperature from about 30° C. to about 90° C., from about 35° C. to about 60° C., or from about 35° C. to about 45° C. In certain embodiments, the thermoset step is conducted at a temperature of at least 30° C. In further embodiments, the thermoset step is conducted at a temperature of at least 40° C. In further embodiments, the thermoset step is conducted at a temperature of at least 45° C. In further embodiments, the thermostep is conducted at a temperature of at least 50° C. In certain embodiments, the activated biological material can be thermoset for a period of time from about 1 minute to about 48 hours, from about 1 minute to about 24 hours, from about 1 minute to about 12 hours, from about 1 minute to about 6 hours, or from about 1 minute to about 2 hours. In certain embodiments, the activated biological material is thermoset for at least 1 minute. In further embodiments, the activated biological material is thermoset for at least 30 minutes. In further embodiments, the activated biological material is thermoset for at least 1 hour. In further embodiments, the activated biological material is thermoset for at least 2 hours. In further embodiments, the activated biological material is thermoset for at least 6 hours. In further embodiments, the activated biological material is thermoset for at least 12 hours. In further embodiments, the activated biological material is thermoset for at least 24 hours. In further embodiments, the activated biological material is thermoset for at least 48 hours.

Ligands may then be bound to the functional hydroxyl groups. Ligands may include coupling agents and pharmacological or bioactive agents. In some embodiments, a coupling agent is used to facilitate bonding (e.g. covalent bonding) between the activated biological material and a pharmacological or bioactive agent (such as an antibiotic). For example, surface reactive groups are bound to a coupling agent. Ligands are then directly conjugated onto the coupling agent biological material conjugate. In a certain embodiment, a coupling agent such as 1,1'-carbonyldiimidazole can be used to create a bond between the activated surface groups and free amine groups and the antibiotic gentamicin. Another coupling agent is a mixture of 1-Ethyl-3-(3-dimethylaminopropyl)carbodiimide (EDCI) and N-Hydroxysuccinimide (NHS). In certain embodiments, the biological material is dehydrated prior to activation and/or ligand binding.

Biological materials used in the method of the present invention are preferably dehydrated prior to modification. This can be achieved through, for example, lyophilization or a solvent exchange process. An exemplary solvent exchange process comprises soaking the biological material in an organic hydrophilic solvent miscible with water, such as ethanol, iso-propanol, or any other azeotrope-forming solvent to extract the water from the biological material. This can be performed for one or more cycles (e.g., 2 or 3 cycles). The tissue can then be soaked in organic solvents with lower boiling points, such as dichloromethane or tetrahydrofuran, for one or more cycles (e.g., 2 or 3 cycles) to replace the previous solvent. After draining out the solvent, the biological material is then dried. In one embodiment, the sample is placed under vacuum with or without gentle heating, to remove any residual solvent that remains.

Intermediary layers (e.g., coupling agents) that may be used to create a series of covalent bonds between the thermoset-activated tissue surface and the further ligand preferably have one or more of the following qualities: (i) in its final processed state it is biocompatible; (ii) it is reactive with the activated tissue substrate upon application; (iii) after application, the intermediary layer is reactive with the bioactive agent or subsequent intermediary layer; and (iv) in its final processed state, it is substantially as flexible as its underlying substrate, which may be achieved, for example, through the thinness of the layer. The intermediary layers may be provided via various ligands, including coupling agents, the inorganic phosphates, or the organic phosphinates or phosphonates.

The ligand can be, e.g., a coupling agent, a pharmacologic agent or bioactive agent, phosphate ligand, organic ligands of carboxylic and phosphoric acids, containing between 2 and 20 carbon atoms, ligands of pi-electron delocalized compounds, and/or combinations thereof. The ligand may be functionalized to promote bonding to biological material. Preferred pi-electron delocalized compounds include aromatic ring compounds, such as, but not limited to, phenolate. Ligands may be saturated or unsaturated, branched or unbranched, substituted or unsubstited, and may be aromatic or non-aromatic.

The carboxylic acid may be a monocarboxylic acid, dicarboxylic acid, or an anhydride of a dicarboxylic acid. Typical carboxylic acids will contain between 2 and 20 carbon atoms (exclusive of each carbonyl carbon), and preferably will contain between 3 and 18 carbon atoms. Stearic acid is one example of a carboxylic acid. A substituted carboxylic acid, for example, may be a halogen-substituted carboxylic acid. Carboxylic acids may be unsaturated, which may be polymerized to form polymeric surface layers on the biological material. Exemplary unsaturated carboxylic acids include vinyl carboxylic acids such as acrylic acids, methacrylic acid, maleic acid, and the like. Halogen-substituted acrylates may, in some embodiments, enable the resulting surface layer to be fully polymerized. Cinnamic acid may also be employed.

Phosphonic acids may be saturated or unsaturated, branched or unbranched, substituted or unsubstituted, and may be aromatic or non-aromatic. Phosphonic acids may include between two and twenty carbon atoms, and in some embodiments, contain between three and eighteen carbon atoms. Stearyl phosphonic acids may also be employed.

Essentially any pi-electron delocalized compound capable of reacting with a transition metal is suitable for use with the present invention, including, without limitation, pi-electron delocalized aromatic ring compounds such as phenol. Five-membered heteroaromatic ring compounds having proton-donating ring substituents capable of reacting with the transition metal are also suitable.

Certain embodiments of the present invention include a composition comprising a biological material and a ligand covalently bound to a surface of the biological material. The biological material may be, for example, soft tissue, collagen, bone, dermal tissue, or any other suitable tissue. In certain embodiments, the biological material is acellular. The ligand can, for example, be a pharmacological agent, a biologically active molecule, or a coupling agent.

In certain embodiments, the present invention includes a composition comprising acellular tissue, a coupling agent bound to the acellular tissue, and pharmacological agent bound to the coupling agent.

The biological material can be derived from any suitable biological source, including, without limitation, mammalian, avian, reptilian, amphibian and bacteria. In certain embodiments, the mammalian source is selected from humans, primates (e.g., monkeys, chimpanzees, gorillas, gibbons and orangutan), livestock (e.g., pigs, cows, horses, goats, sheep), dogs, cats, rabbits, guinea pigs, gerbils, hamsters, rats, and mice. In certain embodiments, the mammalian source is a human cadaver. In other embodiments, the mammalian source is a living human. Examples of avian sources include chicken, turkey, duck and goose.

The biological material is preferably acellular. One source of acellular tissue that can be modified according to the present invention is FlexHD® commercially available from Ethicon. Further examples of acellular biological materials are described in U.S. Patent Application Publication No. 2006/0275377; International Application No. PCT/US08/52882; International Application No. PCT/US08/52884, and International Application No. PCT/US08/52885, which are incorporated herein by reference in their entireties.

In certain embodiments, the biological material is dehydrated. Dehydration can be carried out by, for example, lyophilization or a solvent exchange process. In some embodiments, the biological material has been dehydrated via a solvent exchange process comprising soaking the biological material in a solvent. In further embodiments, the biological material has been dehydrated via a solvent exchange process comprising soaking the biological material in a hydrophilic solvent followed by soaking the biological material in an organic solvent. In some embodiments, the biological material has been dehydrated via a solvent exchange process comprising soaking the biological material in a hydrophilic solvent followed by soaking the biological material in an organic solvent under vacuum.

In a particular embodiment, the solvent exchange process comprises soaking the biological material in a solvent miscible with or capable of forming an azeotrope with water. The biological material can then be optionally placed under a vacuum with or without heat.

In another embodiment, the solvent exchange process comprises soaking the biological material in a solvent miscible with or capable of forming an azeotrope with water followed by soaking the biological material in a volatile organic solvent. Preferably, the boiling point of the organic solvent at atmospheric pressure is less than or equal to about 80° C., less than or equal to about 70° C., or less than or equal to about 80° C. The biological material can then be optionally placed under a vacuum with or without heat.

The solvent for a solvent exchange process used to prepare the biological material of the present invention can be, for example, one or more of ethanol, n-propanol, iso-propanol, n-butanol, sec-butanol, iso-butanol, tert-butanol, allyl alcohol, benzyl alcohol, furfuryl alcohol, cyclohexanol, benzyl alcohol, tetrahydrofuran, chloroform, methyl ethyl ketone, benzene, ethyl acetate, cyclohexane, benzene, carbon tetrachloride, ethylene chloride, acetonitrile, toluene, n-hexane, n-heptane, carbon disulfide, diethyl ketone, n-propyl acetate, methanol, acetone, aqueous mixtures thereof, and combinations thereof. In certain embodiments, the solvent is an organic solvent and can be, for example, one or more of dichloromethane, tetrahydrofuran ethyl ether, methyl t-butyl ether, pentane, hexane, aqueous mixtures thereof, and combinations thereof.

In embodiments that subject the biological material to a solvent exchange process, the biological material may be placed under vacuum at room temperature or with heat.

In certain embodiments of the present invention, the ligand that is bound to the biological material is a coupling agent. The coupling agent can, for example, be 1,1'-carbonyldiimidazole, 1-ethyl-3-[3-dimethylaminopropyl]carbodiimide hydrochloride, N,N'-Disuccinimidyl carbonate, N-hydroxysuccimimidyl chloroformate, isocyanate, Benzotriazol-1-yloxy)tris(dimethylamino) phosphonium hexafluorophosphate, (Benzotriazol-1-yloxy) tripyrrolidinophosphonium hexafluorophosphate, O-(7-Azabenzotriazol-1-yl)-N,N,N',N'-tetramethyluronium hexafluorophosphate, O-(Benzotriazol-1-yl)-N,N,N',N'-tetramethyluronium hexafluorophosphate, O-(Benzotriazol-1-yl)-N,N,N',N'-tetramethyluronium tetrafluoroborate, (7-Azabenzotriazol-1-yloxy)tripyrrolidinophosphonium hexafluorophosphate, 1-Hydroxybenzotriazole, N,N'-Dicyclohexylcarbodiimide, N,N'-Diisopropylcarbodiimide, Diethyl azodicarboxylate or N,N'-Di-tert-butylcarbodiimide, pharmaceutically acceptable salts thereof, derivatives thereof and combinations thereof.

In some embodiments, a second ligand is bound to the composition of the present invention. The second ligand can, for example, be a pharmacological agent that is bound (e.g. covalently bound) to the biological material via the first ligand. The pharmacological agent can be, for example, an antimicrobial agent such as an antibiotic. In certain embodiments, the antibiotic has an available nucleophilic group.

In certain embodiments, the antimicrobial agent is selected from one or more of amikacin, gentamicin, kanamycin, neomycin, netilmicin, tobramycin, paromomycin, geldanamycin, herbimycin, loracarbef, ertapenem, doripenem, imipenemlcilastatin, meropenem, cefadroxil, cefazolin, cefalotin, cefalexin, cefaclor, cefamandole, cefoxitin, cefprozil, cefuroxime, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spectinomycin, spiramycin, aztreonam, furazolidone, nitrofurantoin, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, amoxicillin/clavulanate, ampicillin/sulbactam, piperacillin/tazobactam, ticarcillin/clavulanate, bacitracin, colistin, polymyxin B, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, trimethoprim-sulfamethoxazole, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole, pharmaceutically acceptable salts thereof, derivatives thereof, and combinations thereof.

In certain embodiments, the antimicrobial agent of the present invention is selected from one or more of chlorhexidine, biguanides, quaternary ammonium compounds, pharmaceutically acceptable salts thereof, derivatives thereof, and combinations thereof.

The attachment of the ligand can be performed, e.g., by contact with an aqueous, non-aqueous or partial aqueous solution of the ligand. The solution can contain the ligand, e.g., in an amount from about 0.0001% to about 99% w/w. In particular embodiments, the ligand solution (e.g., gentamicin or 1,1'-carbonyldiimidazole) comprises from about 0.0001% to about 50%, from about 0.001 to about 25%, from about 0.01 to about 10% or from about 0.1 to about 5% ligand.

In certain embodiments, the source of the oxygen plasma can be $O_2$, air, or a combination thereof. In other embodiments, the source of oxygen plasma is any gaseous mixture that has a minimum percent of oxygen to provide a suitable surface of functional groups on the biological material after contact to allow for further chemical modification In certain embodiments, a ligand such as an antimicrobial or antibiotic agent is directly bound to the surface functional groups of the biological material without the use of intermediary layers such as coupling agents.

In certain embodiments, the compositions, biological materials, or activated biological materials are sterilized, i.e., they are substantially free of living microorganisms such as bacteria and viruses.

In certain embodiments of the inventive composition comprising a pharmacological agent, the composition maintains between about 5% and 95% of the pharmacological agent after soaking in an infinite sink in phosphate buffer saline for 24 hours, for 4 days, for 7 days, or for 14 days.

In further embodiments of the inventive composition comprising a pharmacological agent, the composition maintains between about 50% and 95% of the pharmacological agent after soaking in an infinite sink in phosphate buffer saline for 24 hours, for 4 days, for 7 days, or for 14 days.

In other embodiments of the inventive composition comprising a pharmacological agent, the composition maintains at least about 20%, at least about 30%, at least about 40%, at least about 50%, at least about 60%, at least about 70%, at least about 80%, or at least about 90% of the pharmacological agent after soaking in an infinite sink in phosphate buffer saline for 24 hours, for 4 days, for 7 days, or for 14 days.

In further embodiments of the inventive composition comprising a pharmacologic agent, the amount of pharmacological agent is maintained after soaking in an infinite sink in phosphate buffer saline for 4 days, for 7 days, or for 14 days is within about 10%, within about 15%, within about 20%, or within about 25% of the amount of pharmacological agent present in the composition at 24 hours.

The modified biological materials disclosed herein can be used in reconstructive surgery including but not limited to hernia repair, breast reconstruction, abdominal wall repair, chest wall repair, urological repair, bone and cartilage implantation, gynecological repair, plastic surgery, tendon repair, burn and wound treatment and vein/artery repair.

The modified biological materials disclosed herein are optionally packaged in a sterile container for transport and storage.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

Solvent Exchange

FlexHD® samples were immersed in absolute ethanol for 15 minutes with gentle shaking. This step was repeated until a total of 3 cycles had been completed. The samples were then immersed in dichloromethane for 15 minutes with gentle shaking. This step was repeated once more so that a total of 2 cycles were completed. The samples were then placed in a vacuum oven at 30° C. for 1 hour to remove residual solvent.

Example 2

Thermoset Activation

Lyophilized biological material samples, or a sample dehydrated according to Example 1, was cut into 2 cm×6 cm samples and treated with Harrick oxygen plasma for 30 seconds at high radio frequency level (30 W). The samples were then placed in a chemical vapor deposition chamber. The chamber was vacuumed for 3 to 5 hours until the pressure reached about $1\times10^{-3}$ torr. The samples were the exposed to zirconium (IV) tert-butoxide vapor for 20 minutes followed by a gentle heat at 50° C. for 10 minutes. The samples were taken out of the chamber and placed in 10 mg/mL (11-Hydroxyundecyl)-phosphonic acid ethanol solution for 30 minutes. Then the samples were rinsed with absolute ethanol and dried under vacuum. The samples were thermoset at 40° C. for 1 hour under vacuum.

Example 3

Attachment of Coupler to Activated Sample

Immediately after processing according to Example 2, samples were immersed in 50 mL of tetrahydrofuran (THF) containing 175 mg of 1,1'-carbonyldiimidazole (CDI) for 30 minutes in a 50 mL Falcon tube at room temperature to yield samples to which CDI was covalently bound to the samples.

Example 4

Attachment of Antibiotic

The CDI-bound samples of Example 3 were rinsed with THF and immersed in 50 mL of gentamicin sulfate aqueous solution with a concentration of 10 mg/mL at room temperature for 2 hours to covalently bind the gentamicin to the sample. Following gentamicin conjugation, samples were washed extensively with deionized water to remove any unattached gentamicin. They were then soaked in deionized water for 20 minutes followed by another 20 minute soak in 70% ethanol with gentle agitation. The samples were then soaked in PBS overnight for at least 16 hours to remove any unattached gentamicin.

Example 5

Bacterial Outgrowth Assay

An overnight culture of *E. coli* (ATCC 25404) was diluted down to $OD_{600}$ nm=0.03 (approximately $10^6$ CFU/mL) in LB (Lennox) broth (Fisher) and 20 µL of this bacterial dilution was pipetted onto 6 mm biopsy punches of untreated human dermis as a control or thermoset gentamicin-treated dermis (prepared according to Example 4). The samples were incubated for 10 minutes at room temperature before each one was placed into sterile 50 mL Erlenmeyer flask containing 10 mL LB media. The flasks were shaken at 37° C. at 225 RPM in an orbital shaker (Lab-Line), and optical density measurements were taken every hour to monitor bacterial growth until turbidity was achieved or no growth was observed.

Figure 2:
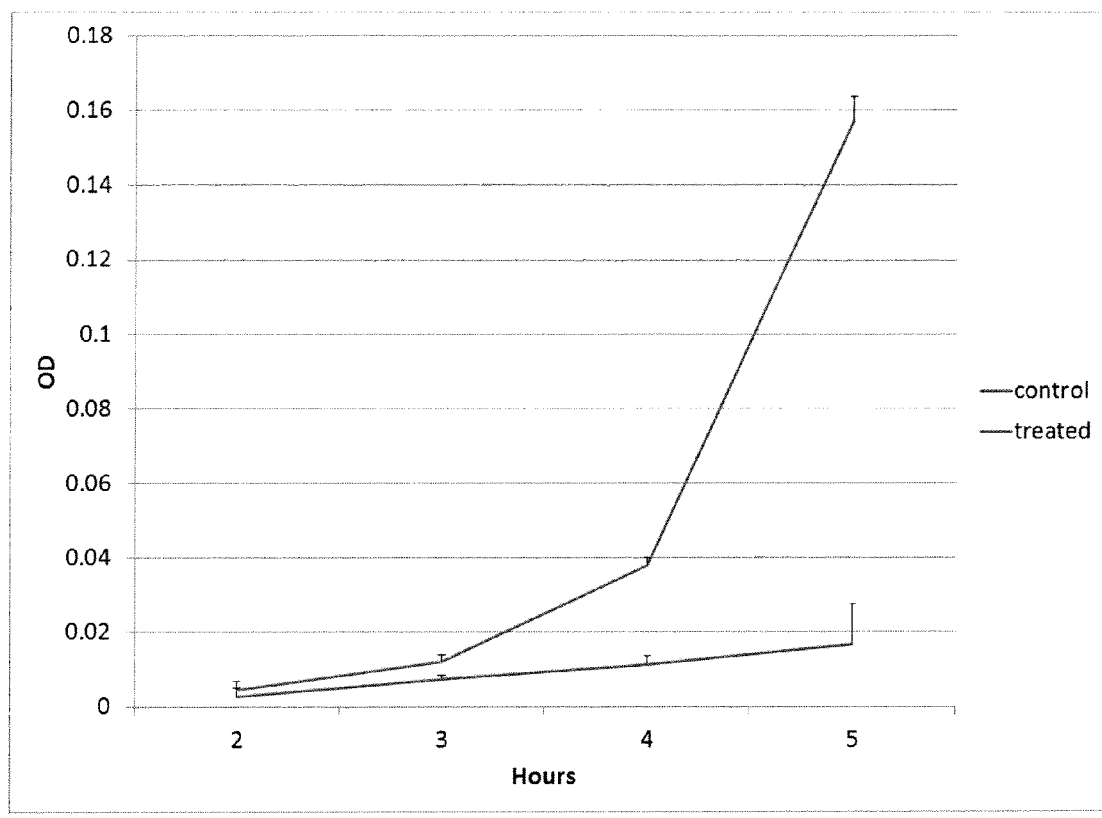
FIG. 2 depicts the results of a bacterial outgrowth assay. N=3 per group, per timepoint. Error bars represent the standard deviation.

As depicted at FIG. 2, at 2, 3, 4, and 5 hours of the outgrowth assay, there were elevated numbers of *E. coli* in the untreated sample compared to the treated sample. The controls samples showed an exponential growth pattern while the treated samples showed attenuated growth which is indicative of nearly complete bacterial eradication during the soaking period.

Example 6

Fibroblast Biocompatibility

Human dermal fibroblasts derived from neonatal foreskin were grown to confluency at 37° C. in a $CO_2$ incubation chamber, in essential media supplemented with 10% Fetal Calf Serum and pen/strep and split in a 1:10 dilution. All studies were performed with passage four cells. Thermoset-treated and control samples were prepared using 6 mm skin biopsy cores to create test samples. The samples were soaked in 70% EtOH for 30 minutes and then placed into essential media for an overnight soak for at least 16 hours. The soak media was aspirated and the samples were placed individually into wells of a 24-well plate and seeded with 10,000 fibroblasts per sample delivered in 50 µL, of complete media. After 30 minutes, an additional 500 µL of complete media was added to each well. Cells were assayed for metabolic activity at 24 hours and 8 days after post-seeding using the TACS MTT assay (Trevigen, Md., USA) according to the manufacturer's instructions. Standard curves were seeded 24 hours prior to performing the MTT assay. For each time point, n=4 treated and control samples were tested. In addition, four treated and control samples were measured for MTT activity without being cell seeded. Readings from these samples were not different between treated and untreated test samples. Therefore, the dermis background to be subtracted from the cell seeding values was determined by averaging these 8 samples together. In previous studies, it was observed that a significant portion of the formazin product was sequestered in the dermis. Therefore, for this study, the media and dermis were assayed separately and background form control dermis was also assayed separately.

Figure 3A:
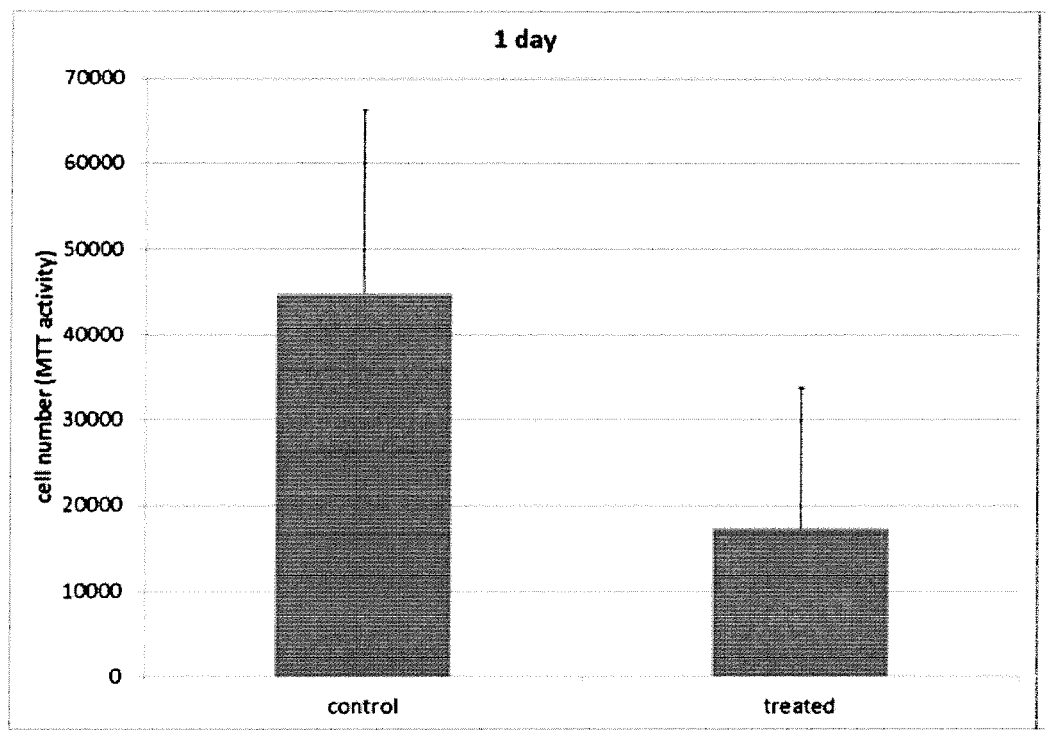
FIG. 3 depicts the cell viability results of a fibroblast assay. N=4 per group. Error bars represent the standard deviation.
Figure 3B:
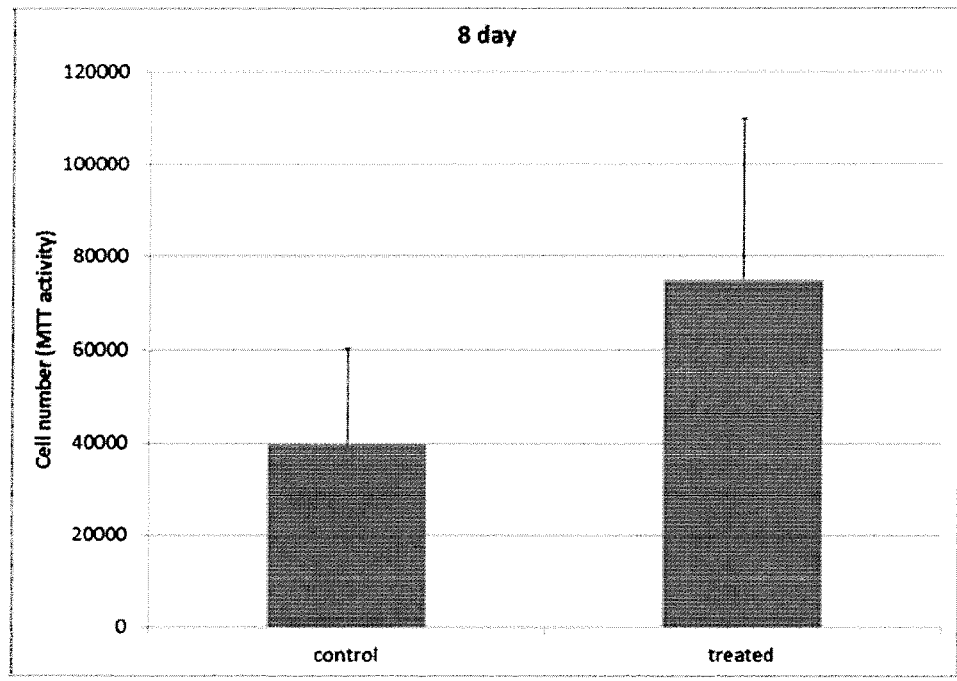
Figure 4:
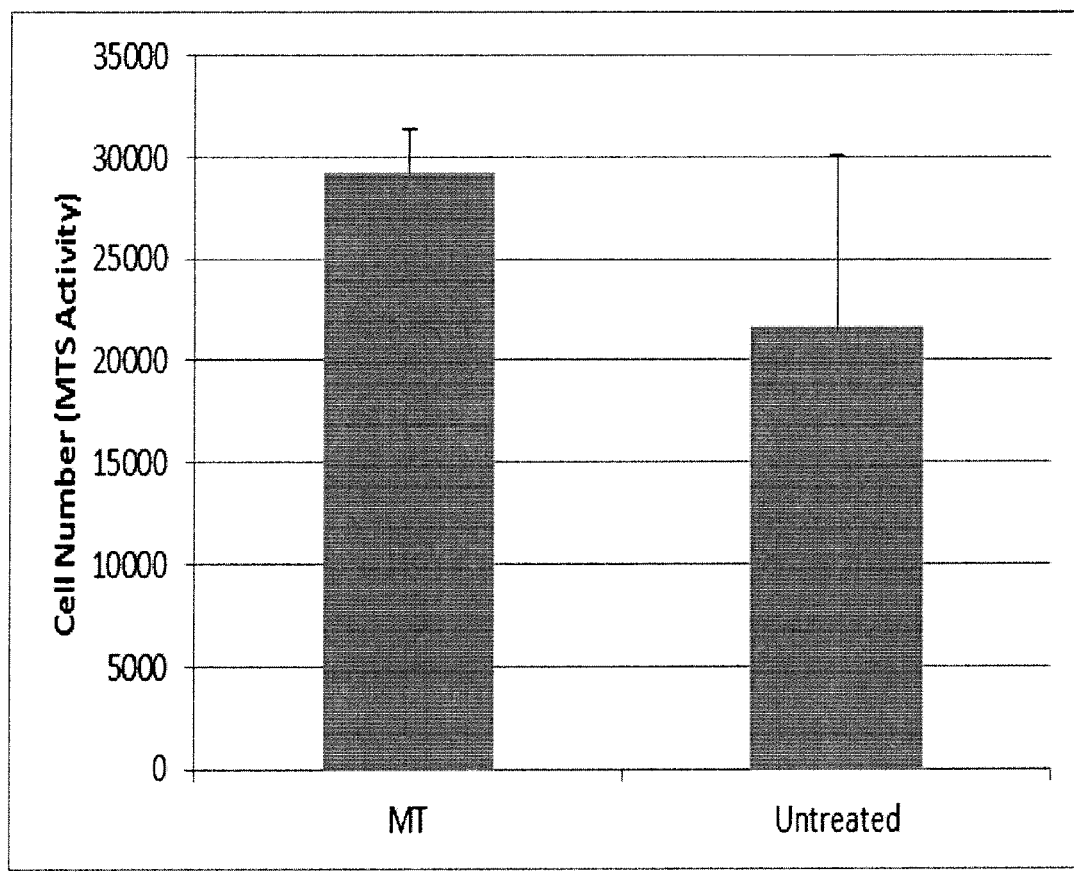
FIG. 4 depicts MTS assay results for thermoset-treated dermis versus untreated dermis at 1 day. N=4 per group. Error bars represent the standard deviation.

The results of the fibroblast assay are shown in FIG. 3. There was no significant different between the treated and control samples at either time point. Although there was variability among samples, there was no evidence that the treatment was preventing cell proliferation on the dermis. At day 1, there was an apparent, although non-significant, decrease in cell attachment. One of the major drawbacks of the MTT assay is loss of color due to interference of the precipitated tetrazolium salt and type I collagen. To address this issue, an MTS assay which uses a water soluble form of the tetrazolium salt, from Promega, was used to repeat the 1 day experiment. The results of that study are shown in FIG. 4. With the MTS assay, there was an improved recovery of colorimetric activity and smaller standard deviations. No evidence of decreased cell attachment or cytotoxicity was noted in this experiment.

Example 7

Cell Viability

Cell viability was assessed at 1 and 4 days of exposure to the dermal matrices. For each timepoint, eight samples from each test groups were placed with the epidermal surface facing up into the wells of a 96 well TCPS plate. The samples were washed with 100 μL of complete media for 5 minutes followed by aspiration of the media and placement of either cells or fresh media without cells onto the samples. For the cell-seeded samples, 10,000 human dermal fibroblasts were seeded onto 4 of the 8 human dermis test samples in 100 μL of complete media.

At the time of initial test sample cell-seeding for the 1 day cell viability samples, a standard curve was prepared in duplicate using the human dermal fibroblasts. To produce the standard curve, 25,000, 12,500, and 6,250 cells were seeded directly onto the TCPS wells. For the 4 day study, the standard curve was prepared three days post cell seeding. The media was exchanged every 24 hours during the study and just prior to the termination of the assay.

The CellTiter 96 Aqueous One Solution Assay (Promega, USA) was used to assess cell viability at 1 and 4 days post cell seeding. The kit was used according to the manufacturer's instruction with a few minor modifications made to accommodate use with human dermis tissue. To each well of the standard curve and the test samples, 20 μL of MTS solution was added. After 90 minutes, the dermis was gently transferred to clean wells leaving the media behind. The colorimetric intensity of each well was measured at 490 nm in both the dermis and media containing wells. The non-cell seeded blanks were averaged together for both the media and dermis and subtracted from the cell-seeded samples to obtain normalized readings. It was necessary to use separate blanks for each of the treatment because it was observed that modifications made to the tissue could change the background color levels of both the media and dermis. The total normalized color observed in the media and dermis was added together and the cell number was determined using the standard curve.

Figure 5:
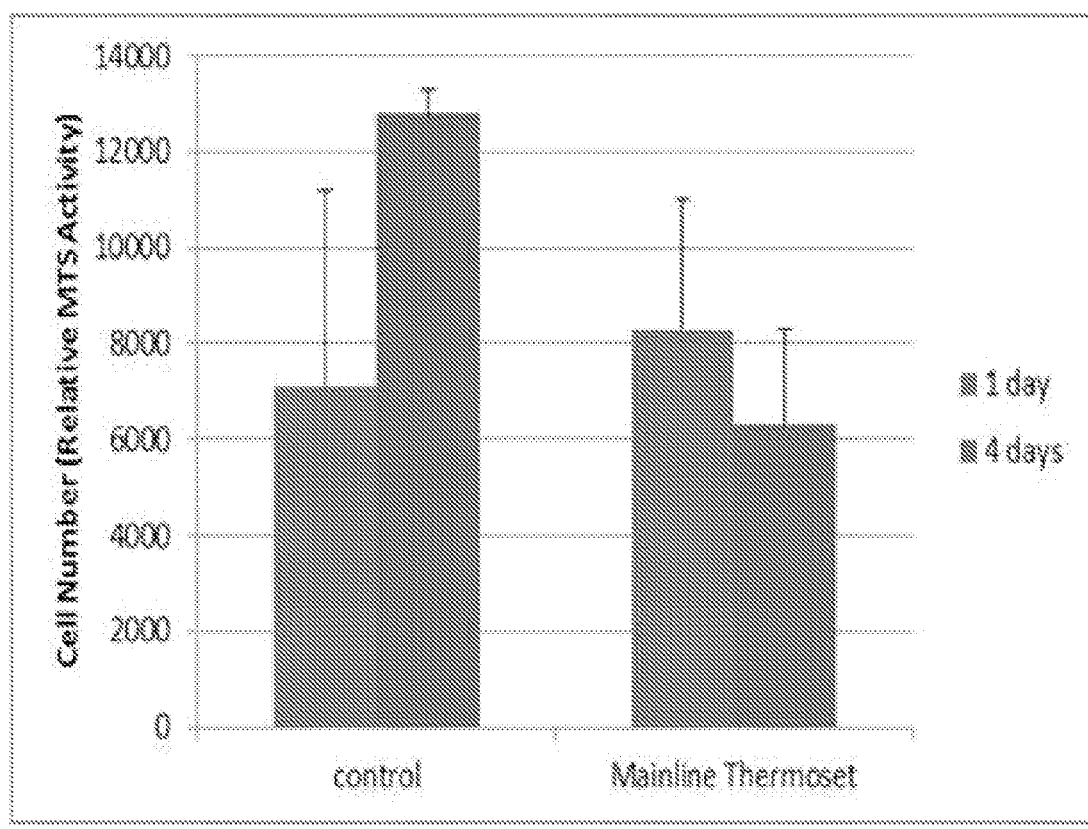
FIG. 5 depicts cell viability results using an MTS assay. Relative cell number was extrapolated from a standard curve produced from dermal fibroblasts grown on TCPS. N=4 for all groups. Error bars represent the standard deviation.

FIG. 5 depicts the results using the MTS assay. Relative cell number was extrapolated from a standard curve produced from dermal fibroblasts grown on TCPS. There was no significant difference between control and thermoset treated samples and controls samples at either point in time.

Example 8

Gentamicin Quantification

The amount of gentamicin loaded into the human dermis was measured in samples prepared as described in Example 7. Three separate dermis samples from the control and thermoset groups were weighed just prior to gentamicin determination. The samples were placed into 5 mL of 0.25M HCl in borosilicate test tubes covered with aluminum foil. The samples were autoclaved at 121° C. with a 1 hour cycle in a Steris autoclave (SG-120 Scientific Gravity Sterilizer) to degrade and solubilize the collagen. In earlier studies, the stability of gentamicin in 0.25M HCl and under autoclave conditions was assessed. No significant loss of gentamicin detection was observed.

Following the autoclave step, the gentamicin was measured using a commercially available ELISA kit (BioO, USA) according to the instruction included in the kit. Human dermis samples were handled according to the protocol as if they were milk samples. Using anticipated drug loads determined from earlier zone of inhibition studies, the autoclaved samples were diluted into 1× sample extraction buffer 1:40. Standards provided with the kit were used to create a standard curve and subsequ3ently to calculate total gentamicin in each sample. The gentamicin load was expressed as parts per million (ppm) by diving the weight of gentamicin by the weight of the dermis sample.

Figure 6:
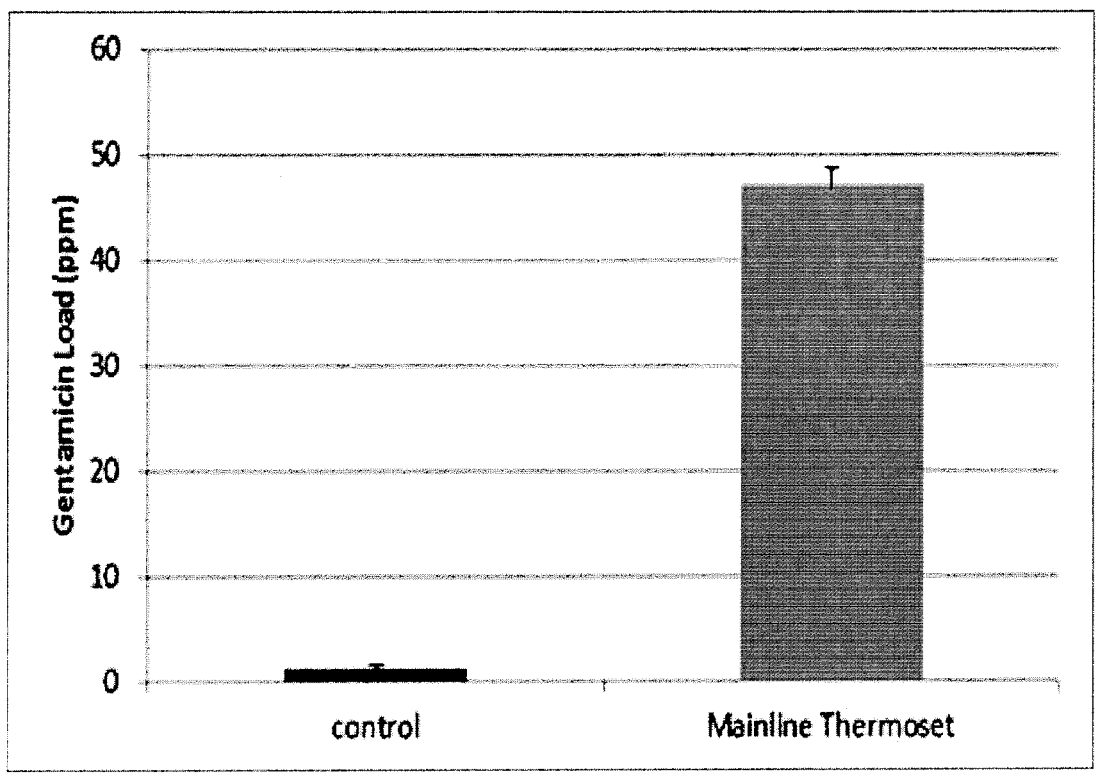
FIG. 6 depicts the results of a gentamicin quantification assay using an ELISA kit. For all groups, n=3. Error bars represent the standard deviation.
Figure 7A:
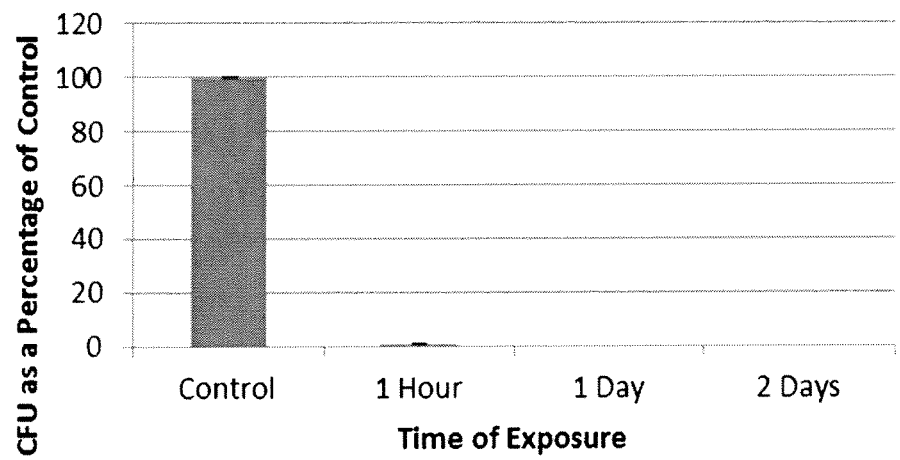
FIG. 7 depicts the percent killing of 4 different bacteria by thermoset-treated samples. For all groups, n=3 and bars represent the standard deviation.
Figure 7B:
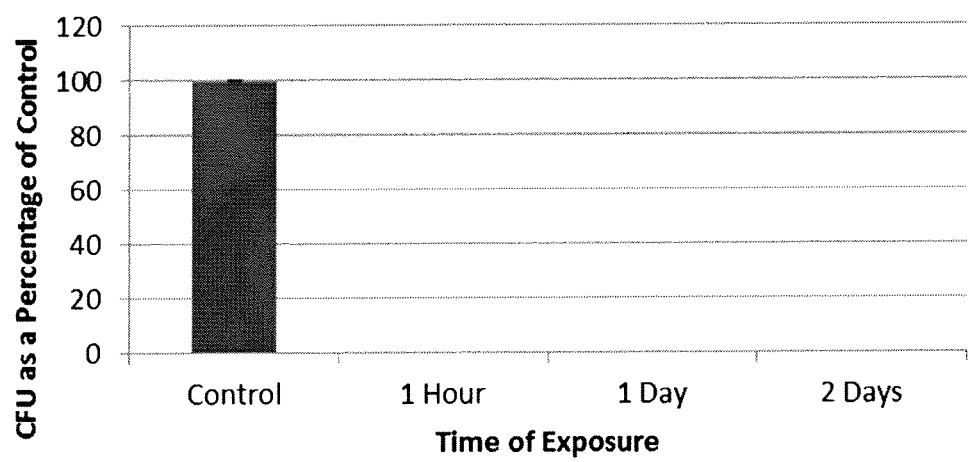
Figure 7C:
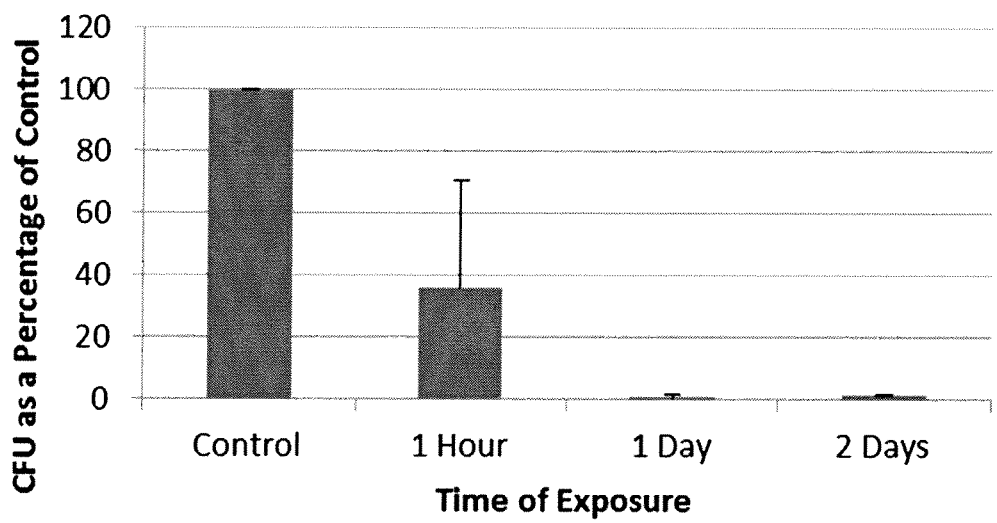
Figure 7D:
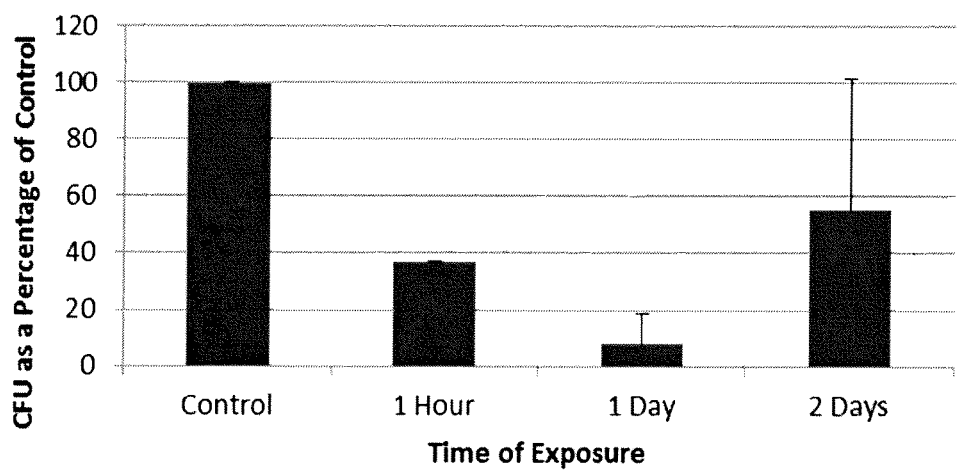

FIG. 6 depicts the results of the assay. Thermoset treated samples contained an average of 47 ppm of residual gentamcin. The control tissue, which did not contain any gentamicin, showed an ELISA value of 0.1 ppm, which represents the baseline background level inherent to the assay.

Example 9

Antimicrobial Activity

The experimental procedure described in the quantitative method of ASTM E2180 was modified and used to evaluate the antimicrobial effectiveness of gentamicin bound to treated and untreated human dermis. The surface area of the test samples was reduced from 3×3 cm squares to 6 mm diameter round dermal biopsy cores. The slurry inoculum volume was reduced from 0.5-1.0 to 6 μL, which provided the required 1 mm depth of slurry across the sample. The neutralizing broth volume was therefore reduced to 600 μL. Finally, the duration of the experiment was increased from 24 hours to 48 hours of exposure of the inoculum to the test surfaces. Consequently, the moisture level of the dermis samples had to be controlled by placing the samples on hydrated squares of sterile filter paper moistened with 200 μL sterile PBS in order to recover viable cells from the untreated samples at 2 days post-slurry inoculation. The filter paper squares were checked form moisture level daily and approximately 200 μL of PBS was added each day.

Briefly, 18 hour bacterial cultures of *S. aureus* (ATCC 25923 and 10390), *E. coli* (ATCC 25404), or *P. aeruginosa* (ATCC 27853) were grown and diluted to $OD_{600}$=1.0, 0.5, 0.5, or 0.5, respectively, in an agar slurry containing 0.85% NaCl and 0.3% agar which was sterilized and equilibrated in a water bath to 45° C. Treated and untreated (control) dermal biopsy cores (in triplicate for each time point) were placed into sterile 35×10 mm petri dishes containing 2.4 $cm^2$ sterile filter papers, and 6 μL of inoculated slurry was pipetted onto each sample. The samples were allowed to gel for 10 minutes at room temperature before 200 μL sterile PBS was pipetted onto the filter paper squares to keep the cores hydrated. The petri dishes were placed into the 37° C. incubator for a specified contact time (1 hour, 1 day, or 2 days). Following the specified contact time, the untreated and treated samples were collected in 600 μl neutralizing broth (TSB for *S. aureus* and *P. aeruginosa*; LB for *E. coli*)

to form a 1:100 dilution of the initial inoculum. The samples were sonicated for 1 min in a non-cavitating sonic bath, followed by 1 min of vigorous mechanical vortexing to release the agar slurry from the samples. Serial dilutions were performed with the neutralizing broth, plated (TSA for *S. aureus* and *P. aeruginosa*; LB for *E. coli*), and incubated overnight at 37° C. Percent reduction was calculated by comparing the CFU recovered from the untreated versus treated samples.

*K. pneumoniae, C. perfringens* and *P. mirabilis* were tested using almost identical conditions with a 24 hour contact time at Gibraltar Labs in Fairfield, N.J. For their studies, all bacteria were cultured for 18 hours and used at OD 0.5 in the agar slurry. The only other difference was that 1 ml was used as the volume for the neutralizing broth in the Gibraltar studies.

The internal ASTM 2180 experiments examined the antimicrobial effects of thermoset treated tissue at three different exposure times (1 hour, 1 day, and 2 days) against *E. coli, P. aeruginosa*, and *S. aureus* 25923 and 10390. The percent killing and log bacterial reduction for the thermoset treated samples are shown below in Table 1, while the percent killing and standard deviation for the themoset treated sample data set are shown in FIG. 7.

TABLE 1

Percent killing and log bacterial reduction for thermoset-treated samples

| Bacterial Species | Percent Killing | | | Log Reduction | | |
|---|---|---|---|---|---|---|
| | 1 Hour | 1 Day | 2 Days | 1 Hour | 1 Day | 2 Days |
| *E. coli* 25404 | 99.6 | 100 | 100 | 2.34 | 4.73 | 5.34 |
| *P. aeruginosa* 27853 | 99.94 | 100 | 100 | 3.46 | 6.13 | 6.64 |
| *S. aureus* 25923 | 64 | 99 | 98.7 | 0.44 | 2.01 | 1.88 |
| *S. aureus* 10390 | 63 | 92.3 | 44.55 | 0.43 | 1.11 | 0.07 |

The external ASTM 2180 experiments performed at Gibraltar Labs in Fairfield, N.J. utilized a single 24 hour (1 day) exposure time of the bacterial slurry on the tissue and three bacterial strains: *Klebsiella penumoniae, Proteus mirabilis*, and *Clostridium perfringens* (vegetative cells). They tested the antimicrobial activity of thermoset treated dermis. The percent killing and log bacterial reduction for these treated samples can be found in Table 2. The treated samples resulted in 99.999% killing with a 5-log reduction of *K. pneumonia*, 99.99% killing with a 4.34-log reduction of *Proteus mirabilis*, and 99.999% killing with a 5.61-log reduction of *C. perfringens*. The treated tissue samples were effective surface antimicrobial against all three of these bacterial species with a 24 hour contact time.

TABLE 2

Percent killing and log bacterial reduction of thermoset-treated dermis against three bacterial strains through external ASTM 2180 testing.

| Bacterial Species | Percent Killing | Log Reduction |
|---|---|---|
| *Klebsiella pneumoniae* | 99.999 | 5 |
| *Proteus mirabilis* | 99.99 | 4.34 |
| *Clostridium perfringens* (vegetative cells) | 99.999 | 5.61 |

Example 10

Bone Tissue Treatment Process

Bone samples were soaked in PBS or 0.9% saline solution at 37° C. for three days. Bone samples were then immersed in 100% ethanol with gentle shaking for 15 minutes. This immersion step was repeated until a total of three cycles had been completed. Finally the bone samples were vacuum dried at room temperature for 2 hours.

The dehydrated bone samples were then treated with oxygen plasma for 30 seconds. Immediately thereafter, the bones were placed in a chemical vapor deposition chamber. The chamber was vacuumed for 3 to 5 hours until the pressure reached about $1\times10^{-3}$ torr. The samples were then exposed to zirconium (IV) tert-butoxide vapor for 20 minutes followed by a gentle heat at 50° C. for 10 minutes. The samples were taken out of the chamber and placed in 10 mg/mL (11-Hydroxyundecyl)-phosphonic acid ethanol solution for 30 minutes. Then the samples were rinsed with absolute ethanol and dried under vacuum. The samples were thermoset at 40° C. for 1 hour under vacuum. Immediately after thermoset processing, samples were immersed in 50 mL of tetrahydrofuran (THF) containing 175 mg of 1,1'-carbonyldiimidazole (CDI) for 30 minutes in a 50 mL Falcon tube at room temperature to yield samples to which CDI was covalently bound to the samples, and then immersed in 10 mg/mL gentamicin sulfate solution for 2 hours. The bone samples were then rinsed with deionized water, soaked in deionized water for 20 minutes, and then soaked in 70% ethanol for 20 minutes. Finally, the bone samples were soaked in PBS for 1 hour.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

We claim:

1. A composition for reducing the risk of infection comprising effective amounts of:
   oxygen plasma-activated acellular dermal tissue,
   transition metal atoms selected from the group consisting of Group IVB, Group VB, Group VIB of the Periodic Chart and a combination thereof, bound to a surface of the activated acellular tissue,
   an inorganic phosphate, organic phosphinate or organic phosphonate bound to the transition metal atoms,
   a coupling agent bound to the inorganic phosphate, organic phosphinate or organic phosphonate, and
   a pharmacological agent bound to the coupling agent,
   wherein when soaked in an infinite sink in phosphate buffer saline for 24 hours, the composition maintains about 5% to about 95% of the pharmacological agent;
   wherein the acellular tissue has less than 3% by weight viable cells based on the total weight of the acellular tissue; and/or
   wherein the acellular tissue has less than 25% by weight nucleic acid based on the total weight of the acellular tissue.

2. The composition of claim 1, wherein the transition metal atoms are selected from the group consisting of titanium, zirconium and a combination thereof.

3. The composition of claim 1, wherein an inorganic phosphate is bound to the transition metal atoms.

4. The composition of claim 1, wherein an organic phosphinate or organic phosphonate is bound to the transition metal atoms.

5. The composition of claim 1, wherein the coupling agent is selected from the group consisting of 1,1'-carbonyldiimidazole, 1-ethyl-3-[3-dimethylaminopropyl]carbodiimide hydrochloride, N,N'-disuccinimidyl carbonate, N-hydroxysuccimimidyl chloroformate, isocyanate, salts thereof, and a combination thereof.

6. The composition of claim 1, wherein the source of oxygen plasma is $O_2$.

7. The composition of claim 1, wherein the source of oxygen plasma is air.

8. The composition of claim 1, wherein when soaked in an infinite sink in phosphate buffer saline for 24 hours, the composition maintains about 50% to about 95% of the pharmacological agent.

9. The composition of claim 1, wherein when soaked in an infinite sink in phosphate buffer saline for 14 days, the composition maintains about 5% to about 95% of the pharmacological agent.

10. The composition of claim 1, wherein when soaked in an infinite sink in phosphate buffer saline for 14 days, the composition maintains about 50% to about 95% of the pharmacological agent.

11. The composition of claim 1, wherein the acellular tissue has less than 1% by weight viable cells based on the total weight of the acellular tissue; and/or wherein the acellular tissue has less than 10% by weight nucleic acid based on the total weight of the acellular tissue.

12. The composition of claim 1, wherein the acellular tissue has less than 0.5% by weight viable cells based on the total weight of the acellular tissue; and/or wherein the acellular tissue has less than 5% by weight nucleic acid based on the total weight of the acellular tissue.

13. The composition of claim 1, wherein the acellular tissue has less than 0.2% by weight viable cells based on the total weight of the acellular tissue; and/or wherein the acellular tissue has less than 2% by weight nucleic acid based on the total weight of the acellular tissue.

14. The composition of claim 1, wherein the phosphate, phosphinate or phosphonate are covalently bound to the transition metal atoms.

15. The composition of claim 7, wherein 11-hydroxyundecyl-phosphonic acid is bound to the transition metal atoms.

16. The composition of claim 7, wherein the phosphate or phosphinate or phosphonate bonded material is thermoset at a temperature of at least about 35° C. for at least 1 minute.

17. The composition of claim 7, wherein the phosphate or phosphinate or phosphonate bonded material is thermoset at a temperature from about 35° C. to about 45° C. for a time period from about 30 minutes to about 2 hours.

18. The composition of claim 1, wherein the pharmacological agent is an antimicrobial agent.

19. The composition of claim 18, wherein the antimicrobial agent is selected from the group consisting of amikacin, gentamicin, kanamycin, neomycin, netilmicin, tobramycin, paromomycin, geldanamycin, herbimycin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, clindamycin, lincomycin, daptomycin, azithromycin, clarithromycin, dirithromycin, erythromycin, roxithromycin, troleandomycin, telithromycin, spectinomycin, spiramycin, aztreonam, furazolidone, nitrofurantoin, amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, penicillin g, temocillin, ticarcillin, amoxicillin/clavulanate, ampicillin/sulbactam, piperacillin/tazobactam, ticarcillin/clavulanate, bacitracin, colistin, polymyxin b, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, trimethoprim-sulfamethoxazole, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole, pharmaceutically acceptable salts thereof, and combinations thereof.

20. The composition of claim 18, wherein the antimicrobial agent is selected from the group consisting of chlorhexidine, biguanides, quaternary ammonium compounds, pharmaceutically acceptable salts thereof, and mixtures thereof.

21. The composition of claim 1, wherein the acellular dermal tissue is derived from a mammalian source.

22. The composition of claim 21, wherein the acellular dermal tissue is derived from a human cadaver.

23. The composition of claim 1, wherein the activated acellular tissue is dehydrated.

24. The composition of claim 23, wherein the activated acellular tissue is dehydrated by a solvent exchange process.

25. The composition of claim 24, wherein the solvent exchange process comprises soaking the activated acellular tissue in a hydrophilic solvent followed by soaking the activated acellular tissue in an organic solvent followed by placing the activated acellular tissue under vacuum.

* * * * *